(12) United States Patent
Josephberg et al.

(10) Patent No.: US 8,235,893 B2
(45) Date of Patent: Aug. 7, 2012

(54) SCLERAL DEPRESSOR

(76) Inventors: Robert G. Josephberg, Yonkers, NY (US); Eduardo Besser, Culver City, CA (US)

( * ) Notice: Subject to any disclaimer, the term of this patent is extended or adjusted under 35 U.S.C. 154(b) by 1268 days.

(21) Appl. No.: 11/864,058

(22) Filed: Sep. 28, 2007

(65) Prior Publication Data

US 2008/0081952 A1    Apr. 3, 2008

Related U.S. Application Data

(60) Provisional application No. 60/847,924, filed on Sep. 29, 2006, provisional application No. 60/868,877, filed on Dec. 6, 2006.

(51) Int. Cl.
*A61B 3/00*    (2006.01)

(52) U.S. Cl. .......................... 600/236; 600/245

(58) Field of Classification Search ............ 606/107, 606/236; 600/235–246, 201, 206, 209, 210, 600/214, 219, 226; 206/363, 370
See application file for complete search history.

(56) References Cited

U.S. PATENT DOCUMENTS

| | | | | |
|---|---|---|---|---|
| 2,555,076 A * | 5/1951 | Crossley | ...................... | 606/107 |
| 2,885,537 A * | 5/1959 | Wood, Jr. | ...................... | 362/119 |
| 4,036,230 A * | 7/1977 | Adams | .......................... | 604/294 |
| 4,257,406 A * | 3/1981 | Schenk | .......................... | 600/219 |
| 4,453,546 A * | 6/1984 | Katz et al. | ....................... | 606/1 |
| 5,092,314 A * | 3/1992 | Zeitels | ......................... | 600/194 |
| 5,433,190 A * | 7/1995 | Sunalp | ......................... | 600/236 |
| 5,971,977 A * | 10/1999 | Korenfeld | ........................ | 606/1 |
| 6,440,065 B1 * | 8/2002 | Hered | ......................... | 600/236 |
| 6,544,169 B2 * | 4/2003 | Putrino et al. | ................. | 600/236 |
| 6,675,482 B1 * | 1/2004 | Gilbert et al. | .................. | 30/141 |
| 7,131,982 B1 * | 11/2006 | Karapetyan | .................. | 606/167 |
| 2002/0103496 A1* | 8/2002 | Harper et al. | ................. | 606/169 |
| 2009/0076513 A1* | 3/2009 | Szanto | ............................ | 606/87 |

* cited by examiner

*Primary Examiner* — Kevin T Truong
*Assistant Examiner* — Christopher Beccia
(74) *Attorney, Agent, or Firm* — Cozen O'Connor

(57) ABSTRACT

A scleral depressor designed to better control the globe of the eye is disclosed. In a preferred embodiment, the scleral depressor has a handle and a blade attached to the handle where the blade is a portion of an oblate spheroid. In one embodiment, the blade has an illuminating device. The handle is attached to the blade at an angle or straight in relation to the plane of the handle. In another embodiment, the blade is attached to a thimble. In another embodiment of the invention, the blade has an access hole for simultaneous use of other instruments during examination or surgery. The resulting apparatus has greatly improved control of the eye, effective visualization of the periphery, ease of use for the examiner, and increased comfort for the patient.

18 Claims, 5 Drawing Sheets

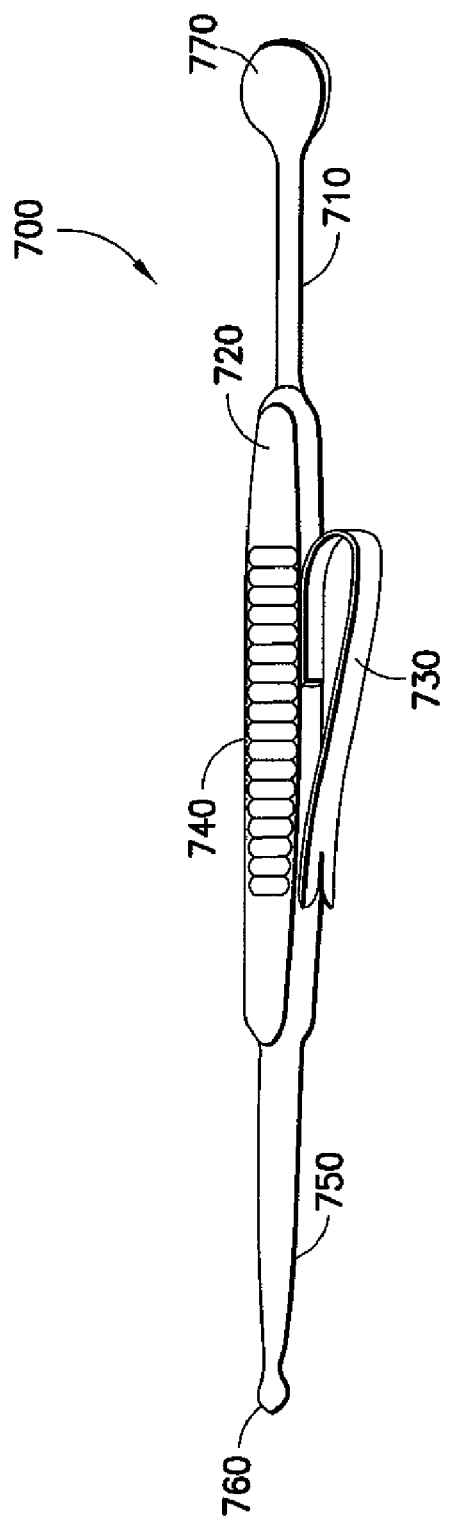
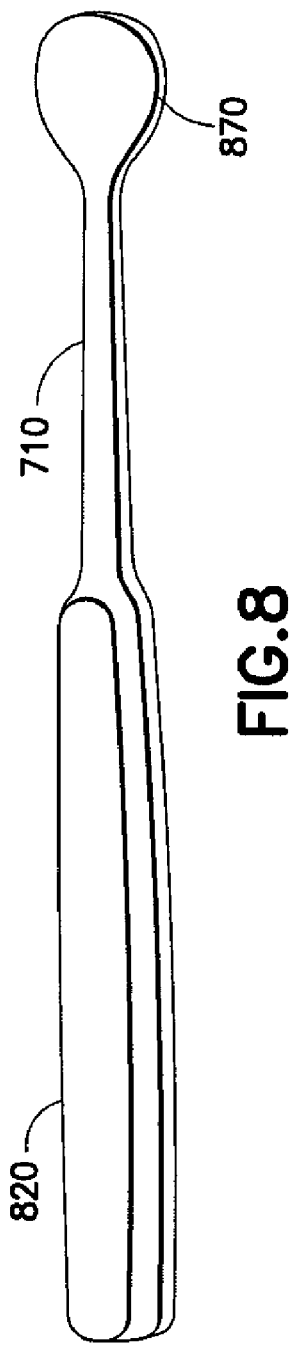
FIG.7
FIG.8

SCLERAL DEPRESSOR

CROSS-REFERENCE TO RELATED APPLICATION

This application claims priority to U.S. Provisional Application No. 60/847,924, which was filed on Sep. 29, 2006, and U.S. Provisional Application No. 60/868,877 which was filed on Dec. 6, 2006, and both are incorporated herein by reference in their entirety.

FIELD OF THE INVENTION

The present invention relates to an ophthalmic surgical and examination tool used for depressing the sclera during an eye examination. More particularly, the present invention relates to a scleral depressor that provides improved manipulation and control over eye position.

BACKGROUND OF THE INVENTION

A scleral depressor is used to facilitate examination of a fundus of an eye, particularly its periphery. During an ocular fundus examination, and particularly during the study of areas of the retina such as the periphery, it is necessary to control the position of the eye. Several sclera depressors have been designed for this purpose. For example, the Storz Instrument Company catalog illustrates several such depressors. These scleral depressors include bulbous or ball end depressors, T-bar depressors, ring depressors, and flat spatula depressors.

The instruments disclosed in the prior art comprise a handle, with optional pocket clip, which is attached to the blade either straight or at an offset angle to facilitate manipulation of the blade from a position that leaves the field substantially clear for the simultaneous use of other instruments, such as an opthalmoscope.

U.S. Pat. No. 4,453,546 discloses a scleral depressor for controlling eye position that has a substantially oblong-shaped blade. The blade has a textured surface with a hole substantially in the middle of the blade. In operation, the blade is manipulated by the operator to depress against the sclera of a patient's eye for either rotating or immobilizing the globe of the eye during examination.

U.S. Pat. No. 6,440,065 discloses an eyelid speculum and scleral depressor for controlling eye position by pressing against the sclera of the eye with a depressor. The scleral depressor has an elongated handle portion, two stem portions and two blades. The blades are flat and substantially paddle-shaped.

In addition to these more conventional prior art devices, some unconventional means, such as paper clips, safety pins, cotton tipped applicators and strabismus hooks are used for the above stated purposes. These type of scleral depressors are not ideally suited for examination for the following general reasons: (a) the tips of these depressors are bulky and with a pediatric lid speculum in place it is often difficult to find adequate room to insert an instrument into the conjunctival sac; (b) undue pressure on the globe and compromise of the ocular circulation is therefore possible; and (c) these scleral depressors have smooth surfaces, slide on the globe, and will not rotate it to different examination positions.

Additionally, both the conventional and unconventional scleral depressors are often difficult to use in conjunction with other instruments because they are not designed for operation from a position which will leave the field substantially clear for the simultaneous use of these instruments in the examination of the eye.

BRIEF SUMMARY OF THE INVENTION

There is a need to make a scleral depressor that can not only maintain good control of the globe of the eye and provide adequate visualization of the periphery, but is also easy to use for the examiner and comfortable for the patient.

A scleral depressor designed to better control the globe of the eye is disclosed. In a preferred embodiment, the scleral depressor has a handle and a blade attached to the handle where the blade is a portion of an oblate spheroid. In one embodiment, the blade has an illuminating device. The handle is attached to the blade at an angle or straight in relation to the plane of the handle. In another embodiment, the blade is attached to a thimble. In another embodiment of the invention, the blade has an access hole for simultaneous use of other instruments during examination or surgery. The resulting apparatus has greatly improved control of the eye, effective visualization of the periphery, ease of use for the examiner, and increased comfort for the patient.

BRIEF DESCRIPTION OF THE DRAWINGS

For the purposes of illustrating the present invention, there is shown in the drawings a form which is presently preferred, it being understood however, that the invention is not limited to the precise form shown by the drawing in which:

FIG. 7 is an orthogonal view of a double ended scleral depressor;

FIG. 8 is an orthogonal view of a double ended scleral depressor;

DETAILED DESCRIPTION OF THE INVENTION

During fundus examination, the slender oblong curved blade of the disclosed scleral depressor can be easily positioned around the globe, whether over the eyelid, along the crease when examining the superior and inferior peripheral retina, or directly on the globe in the medial or lateral conjunctival sac when evaluating the medial or temporal peripheral fundus. The oblong curved blade is wider than the T-bar tip or bulbous end of conventional scleral depressors. Thus, it indents a larger surface area in the peripheral retina allowing visualization of a wider field with less manipulation of the globe. In a preferred embodiment, the oblong curved blade is substantially between 1/8 of an inch and 1 inch wide and between 1/8 of an inch and 1 inch long. In a preferred embodiment, the oblong curved blade is 1/4 inch wide and 3/4 inch long.

Figure 1:
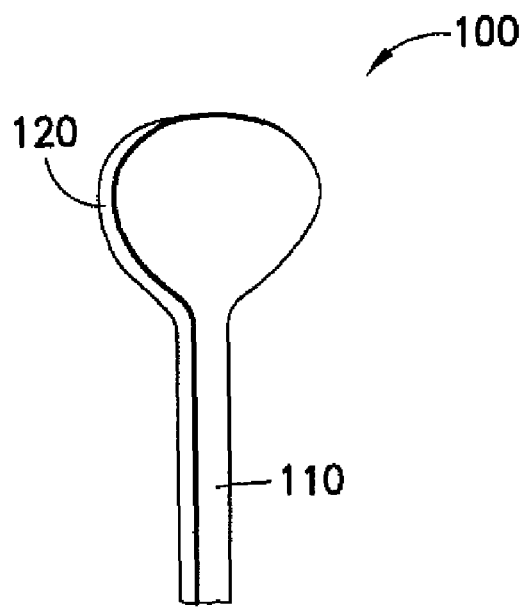
FIG. 1 is a front elevational view of a portion of the depressor.

FIG. 1 illustrates a front elevational view of the scleral depressor 100, comprising a blade 120 and a handle portion 110. In this embodiment of the invention the blade 120 is in a portion of an oblate spheroid, which is attached to the handle portion 110. In one embodiment, the partially spheroid oblate shaped blade 120 has a smooth curved surface. The partially spheroid oblate shaped blade 120 is preferably angled relative to the handle portion 110 to allow manipulation of the partially spheroid oblate shaped blade 120 from an offset position.

During fundus examination, the partially spheroid oblate shaped blade 120 can be positioned easily around the globe or over the eyelids along the lid creases when examining the superior and inferior peripheral retina. The partially spheroid oblate shaped blade 120 can also be placed directly on the medial or lateral conjunctival sac to maneuver and hold the globe in place when evaluating the medial or temporal peripheral fundus. Due to the configuration of the partially spheroid oblate shaped blade 120, the globe can be held effectively into the desired position by the examiner without causing discomfort to the patient such as that caused by other scleral depressors.

The partially spheroid oblate shaped blade 120 has more surface area than a T-bar tip and allows visualization of a wider field without excessive manipulation of the globe. The angled attachment of the partially spheroid oblate shaped blade 120 to the handle portion 110 also provides a substantially clear field during examination.

Figure 2:
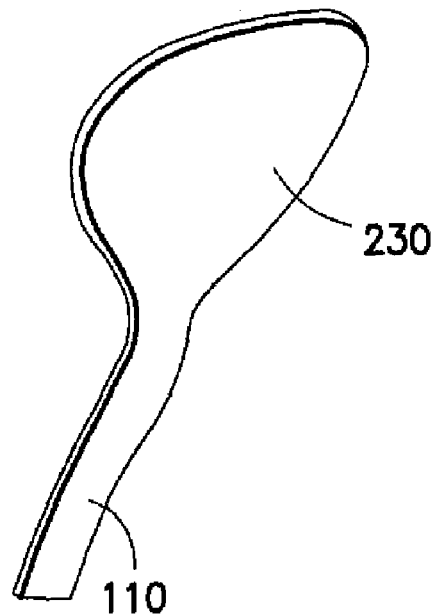
FIG. 2 is an orthogonal view of a portion of the rear of the depressor.
Figure 3:
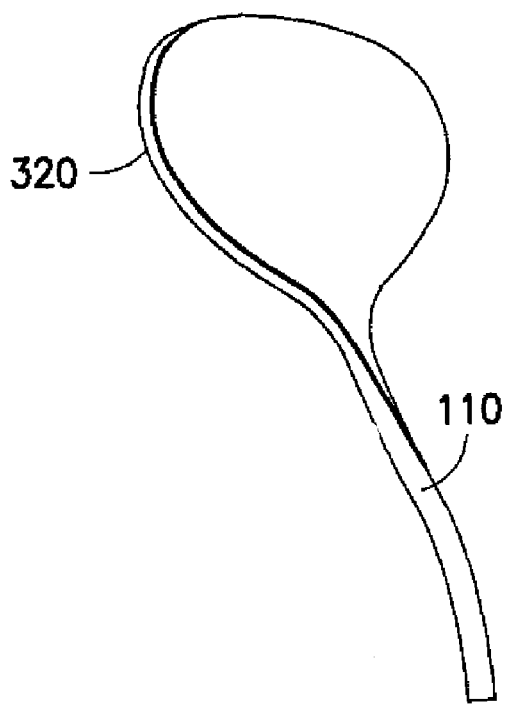
FIG. 3 is an orthogonal view of a portion of the front of the depressor.

Referring now to FIG. 2 and FIG. 3, two views of the embodiment of FIG. 1 are shown. FIG. 2 illustrates an orthogonal view of a portion of the rear of the scleral depressor 100, depicting a rear blade portion 230 and a handle portion 110. FIG. 3 illustrates an orthogonal view of a front portion of the scleral depressor 100, comprising an front blade portion 320 and a handle portion 110. In one embodiment of the invention, the partially spheroid oblate shaped blade is connected to the handle via a curved connector.

Figure 4:
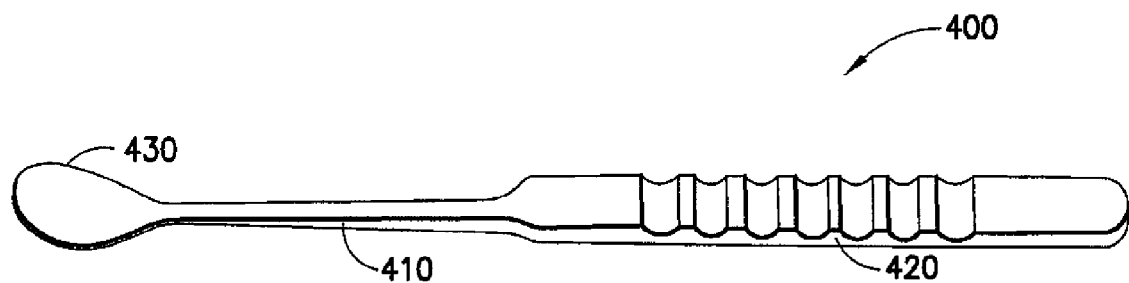
FIG. 4 is a front orthogonal view of a scleral.

In another embodiment, illustrated in FIG. 4, scleral depressor 400 comprises a blade portion 430, a stem 410, and a handle portion 420. As depicted in FIG. 4, stem 410 joins the blade portion 430 and the handle portion 420. In this embodiment, the scleral depressor 400 is a single-tipped instrument attached to a straight handle 420. In another embodiment, the stem 410 creates an angle between the blade portion 430 and the straight handle 420. In a preferred embodiment, the stem 410 is narrow providing a larger field of view.

Handle portion 420 is designed for use during examination, the operating room, and for scleral depression under a microscope. The stem 410 easily slides under a speculum avoiding the use of cotton swabs, muscle hooks, or other devices. Such a configuration makes depression faster, easier and safer. In one embodiment, the handle portion 420 is serrated for easier handling.

Figure 5:
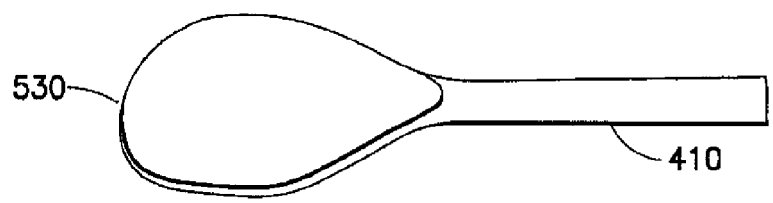
FIG. 5 is a rear elevational view of a portion of the scleral depressor.
Figure 6:
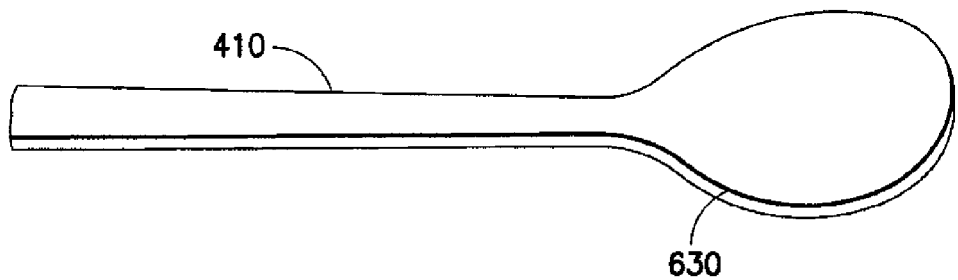
FIG. 6 is a front elevational view of a portion of the scleral depressor.

Referring now to FIG. 5 and FIG. 6, two different views of the embodiment of FIG. 4 are shown. FIG. 5 is a rear elevational view of a portion of the scleral depressor 400, comprising a partially spheroid oblate shaped blade 530 and a stem 410. Whereas, FIG. 6 is a front elevational view of a portion of the scleral depressor 400, comprising a partially spheroid oblate shaped blade 630 and a stem 410.

In an embodiment as shown in FIG. 7, scleral depressor 700 comprises a blade portion 770, a first stem 710, a handle portion 740, a pocket clip 730, a second stem 750, and a bulbous end 760. As depicted in FIG. 7, the scleral depressor 700 is double-ended. In this embodiment of the invention, the blade portion 770 is a blade that is a portion of an oblate spheroid attached to the first stem 710. The first stem 710 is connected to a first end of handle portion 740.

The other end of handle portion 740 is to the second stem 750 which connects to a bulbous end 760. It should be noted that while a bulbous end is shown, the second end of the scleral depressor can be a T-bar depressor, a spatula, or another blade that is a portion of an oblate spheroid. In one embodiment, the scleral depressor has blades that are a portion of an oblate spheroid at both ends, each being a different size. A pocket clip 730, attached to the handle portion 740 of the scleral depressor. This pocket clip 730 can not only be attached to examiner's clothing when scleral depressor 700 is not being used but it can also aid the examiner in stabilizing and controlling the manipulation of scleral depressor 700, for example, by inhibiting unwanted rotation of the handle portion 740.

FIG. 8 is an orthogonal view of a scleral depressor 700 where only one end of the scleral depressor is shown. FIG. 8 comprises a larger blade portion 870, a first stem 710, and a handle 820. As shown in the drawings the first stem 710 is rigidly attached to one end of handle 820 by any suitable means. In one embodiment, the entire scleral depressor is cast as a single piece. In another embodiments the handle and blade ends are cast separately. The handle and blade ends are then attached by suitable methods including welding, soldering, pressure fitting, screws, epoxy, or the like. In this manner, if a component of the scleral depressor is damaged, the damaged portion can be replaced.

Figure 9:
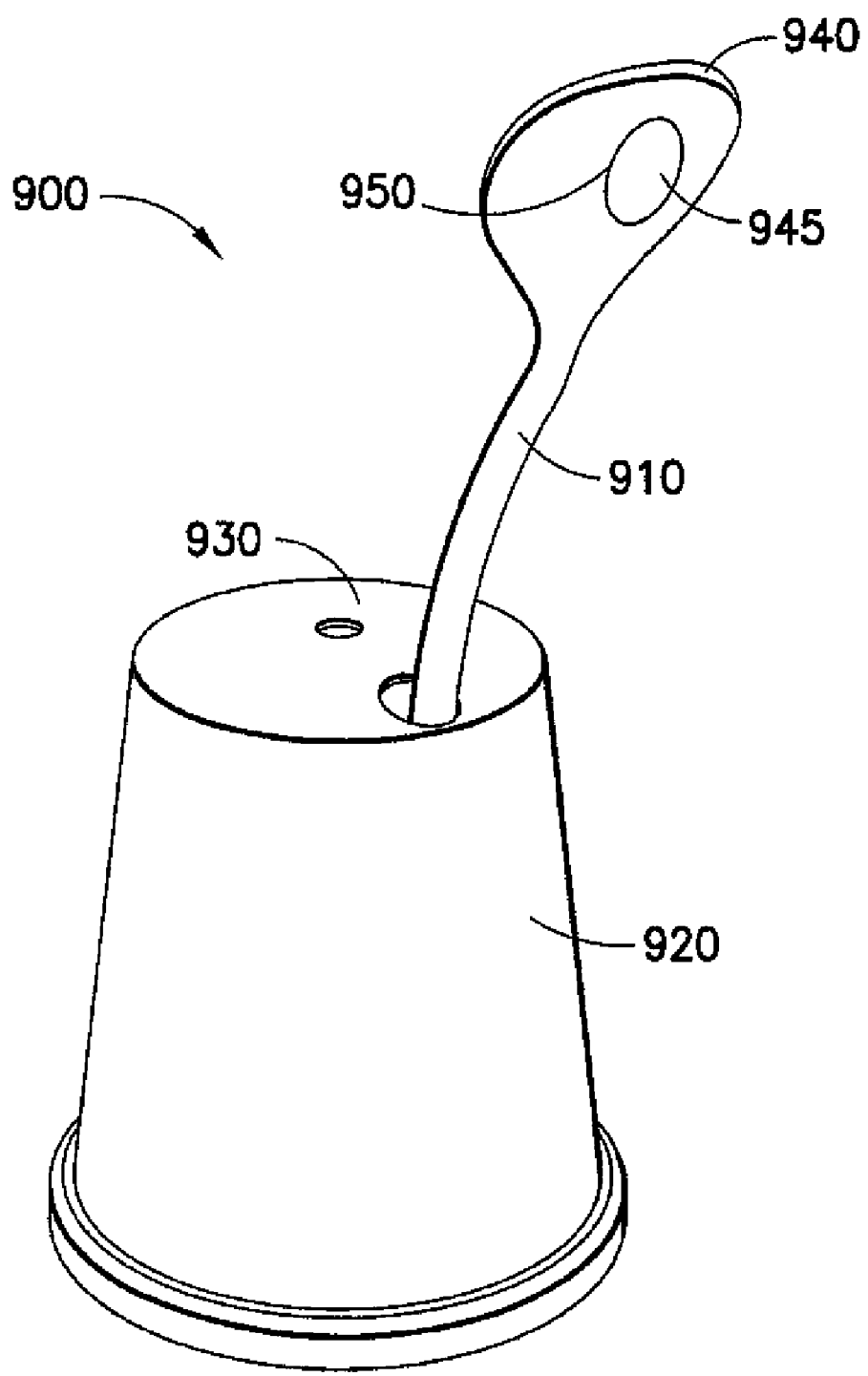
FIG. 9 is an orthogonal view of a thimble scleral depressor.

FIG. 9 depicts an orthogonal view of a thimble scleral depressor 900. The scleral depressor 900 includes a partially spheroid oblate shaped blade 940 that is a portion of an oblate spheroid. The partially spheroid oblate shaped blade 940 is attached to an extension portion 910. The extension portion 910 is attached to thimble 920 at the end opposite the partially spheroid oblate shaped blade 940. The partially spheroid oblate shaped blade 940 in this embodiment is angled relative to the extension portion 910 to allow manipulation of the partially spheroid oblate shaped blade 940 from an offset position.

The partially spheroid oblate shaped blade 940 has a smooth curved surface. In another embodiment, the partially spheroid oblate shaped blade 940 is textured or coated with diamond dust to the like to increase the coefficient of friction of the blade. The partially spheroid oblate shaped blade 940 conforms to the curvature of the eye. The partially spheroid oblate shaped blade 940 is made to generally match the shape of the human eye. Due to the shape of the partially spheroid oblate shaped blade 940, it does not slide on the sclera of the eye during examination and provides easier scleral depression.

As illustrated in FIG. 9, the scleral depressor has a hole 945 in the blade. This hole 945 can facilitate in gripping and gaining control of the eye during an examination or during surgery. Additionally, surgical tools can also be inserted through access hole 945 during examination or surgery of an eye. In one embodiment, an LED or other light source is integrated into the blade 940 of the scleral depressor 900. This provides improved illumination in the operating room. In one embodiment, a light ring 950 arranged substantially around the access hole 945 illuminates the relevant field. Alternatively, the light ring is provided about the periphery of the blade 940. In another embodiment, a light source 930 provides illumination. In yet another embodiment, the curved tip of the scleral depressor is illuminated using fiber optics or the like.

Any embodiment of this invention can further be used for veterinary applications. In any embodiment of this invention the scleral depressor can be metal, plastic, carbon fiber, or the like. Further, various features of each embodiment can be combined. Additionally, in one embodiment, the tool is partially flexible to conform exactly to the human eye.

Because of the ease of use of the scleral depressor in any of the embodiments described above, an examiner with beginner skill level can also use this tool effectively in performing funduscopy. Further, the disclosed depressor fits easily into lid creases. The shape provides a broader field of depression and is more efficient than T-bars.

Figure 10:
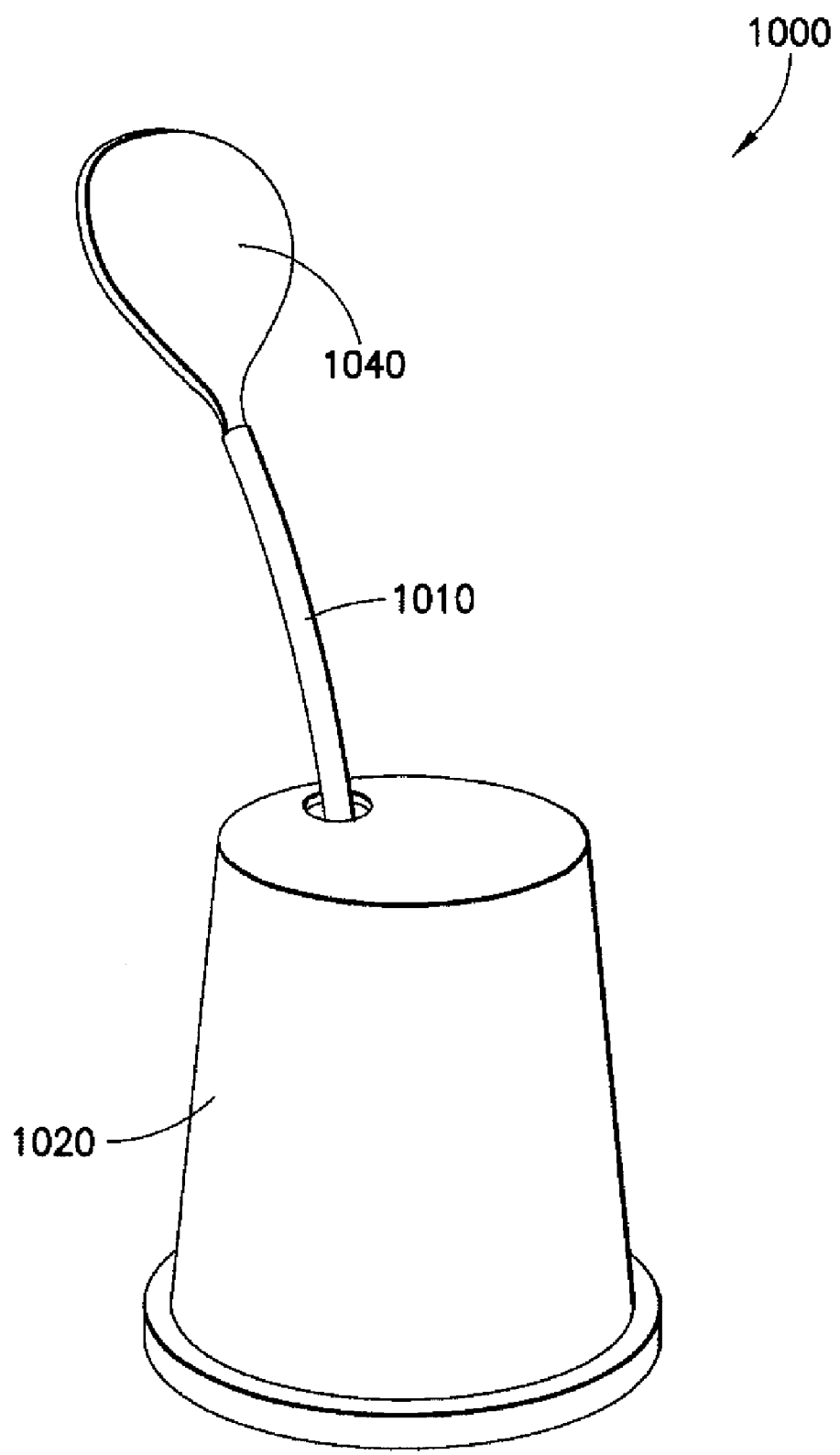
FIG. 10 is an orthogonal view of a thimble scleral depressor.

FIG. 10 is another orthogonal view of a thimble scleral depressor 1000. FIG. 10 comprises a blade 1040 that is a portion of an oblate spheroid attached to an extension portion 1010, and a thimble portion 1020. Extension portion 1010 can be straight, curved, bent, or the like.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed is:

1. A scleral depressor comprising:
holding means having a first and a second end; and
a first blade having a first concave side and a second convex side opposite the first concave side, the blade being attached to the first end of the holding means,
wherein the first blade is a portion of an oblate spheroid shape curved substantially about a longitudinal axis of the scleral depressor to correspond to a contour over an eyelid, along a crease when examining a superior and inferior peripheral retina.

2. The scleral depressor of claim 1, wherein the holding means is a handle.

3. The scleral depressor of claim 1, wherein the holding means is a thimble.

4. The scleral depressor of claim 1, further comprising a second blade attached to the second end of the holding means, wherein the second blade is a portion of an oblate spheroid shape.

5. The scleral depressor of claim 1, wherein the first blade has a smooth surface.

6. The scleral depressor of claim 1, further comprising an illuminating device configured to illuminate an eye under examination.

7. The scleral depressor of claim 2, wherein the handle is narrow at a point joining the first blade to the handle.

8. The scleral depressor of claim 2, further comprising a pocket clip is attached to the handle on a same plane as the first blade and the handle.

9. The scleral depressor of claim 2, wherein the handle is a serrated handle.

10. The scleral depressor of claim 2, wherein the holding means is attached to the first blade in an angled position.

11. The scleral depressor of claim 2, wherein the holding means is attached to the first blade in a straight position.

12. The scleral depressor of claim 3, wherein there is an access hole in the first blade.

13. The scleral depressor of claim 1, wherein the scleral depressor is made of metal.

14. The scleral depressor of claim 1, wherein the scleral depressor is made of plastic.

15. The scleral depressor of claim 1, wherein the scleral depressor is made of carbon fiber.

16. The scleral depressor of claim 1, wherein the first blade is at least 1/8 of an inch wide.

17. The scleral depressor of claim 16, wherein the first blade is at least 1/8 of an inch long.

18. The scleral depressor of claim 4, wherein the second blade has a first concave side and a second convex side opposite the first concave side.

* * * * *